United States Patent
Lo et al.

(10) Patent No.: US 6,207,961 B1
(45) Date of Patent: *Mar. 27, 2001

(54) LOSS COMPENSATION USING DIGITAL-SIGNAL PROCESSING IN FIBER-OPTIC FLUORESCENCE SENSORS

(75) Inventors: K. Peter Lo, Blacksburg, VA (US); Howard P. Groger, Gainesville, FL (US); Shufang Luo, Blacksburg; Russell J. Churchill, Radford, both of VA (US)

(73) Assignee: American Research Corporation of Virginia, Radford, VA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/950,746

(22) Filed: Oct. 15, 1997

Related U.S. Application Data

(60) Provisional application No. 60/028,389, filed on Oct. 15, 1996.

(51) Int. Cl.[7] .................................................. G01N 21/64
(52) U.S. Cl. .......................................................... 250/459.1
(58) Field of Search ........................................ 250/459.1

(56) References Cited

U.S. PATENT DOCUMENTS

| | | |
|---|---|---|
| 4,752,115 | 6/1988 | Murray, Jr. et al. . |
| 5,030,420 | 7/1991 | Bacon et al. . |
| 5,151,603 * | 9/1992 | Nakamura ........................ 250/458.1 |
| 5,470,155 * | 11/1995 | Jensen ................................ 374/161 |

OTHER PUBLICATIONS

G. Murtaza and J.M. Senior, "Referencing Strategies for Intensity Modulated Optical Fibre Sensors: a Review," Optics and Laser Technology, vol. 25, No. 4, pp. 235–245, 1993.

J.M. Senior and G. Murtaza, "LED Spectral Slicing Strategies for Enhanced Dual–wavelength Referencing of Intensity Sensors," Microwave and Optical Technology Letters, vol. 9, No. 2, pp. 95–98. Jun. 1995.

M.J.P. Leiner, "Luminescence Chemical Sensors for Biomedical Applications: Scope and Limitations," Analytica Chimica Acta, vol. 255, pp. 209–222, 1991.

R.J. Watts and G.A. Crosby, "Spectroscopic Characterization of Complexes of Ruthenium (II) and Iridium (III) with 4,4'–Diphenyl–2,2'– bipyridine and 4,7'–Diphenyl–1, 10–phenanthroline," Journal American Chemical Society, vol. 93, pp. 3184–3188, Jun. 1971.

* cited by examiner

Primary Examiner—Constantine Hannaher
(74) Attorney, Agent, or Firm—James Creighton Wray; Meera P. Narasimhan

(57) ABSTRACT

An optical fiber fluorescence sensor system capable of compensating fiber bending loss is provided. The system uses a modulated light-emitting diode and digital-signal processing chips to enhance the measurement of fluorescence signals. A fiber-optic oxygen sensor system suitable for measuring oxygen levels in gas and in aqueous media is provided. The system alleviates fiber bending loss. Detection of the signal-to-noise ratio of the system which exceeds 30 dB is done by using inexpensive components.

21 Claims, 3 Drawing Sheets

Without Signal Averaging

With 8 Times Signal Averaging

LOSS COMPENSATION USING DIGITAL-SIGNAL PROCESSING IN FIBER-OPTIC FLUORESCENCE SENSORS

This application claims the benefit of Provisional U.S. Application No. 60/028,389 filed Oct. 15, 1996.

This invention was made with Government support under 93-33610-9096 awarded by the Department of Agriculture. The Government has certain rights in this invention.

BACKGROUND OF THE INVENTION

Fiber-optic sensors have been extensively developed for many applications over the past two decades. Chemical sensors utilizing optical fibers may be fabricated from single or multimode fibers, and may be used for measurement of gases, ions, pH and organic chemicals.

The use of optical fiber as an extrinsic sensor (in which an optical fiber is only used as a transportation medium for light) for oxygen concentration presents a unique opportunity in environmental monitoring, biotechnology process control and aquaculture process control. When compared with Clark-type oxygen sensors, fiber-optic oxygen sensors have the advantage of fast response time, light weight, remotely operable, low maintenance and potentially low cost. However, the use of fluorescence intensity in a fiber-optic oxygen sensor is hampered by problems associated with optical fiber bending loss.

Recent progress in referencing techniques for intensity based optical fiber sensors has been reviewed by MURTAZA and SENIOR, and ratiometric technique such as dual-wavelength referencing configuration has been used to reduce the effect of fiber bending loss.

SUMMARY OF THE INVENTION

The invention uses a spectral slicing method in alleviating the bending loss in a fluorescence intensity based fiber-optic oxygen sensor.

Instead of using the same light source, one detector channel is used to detect the intensity of the light source while the other detector channel is used to detect the intensity of the fluorescent signal.

Digital-signal processing (DSP) technique was implemented to isolate the modulated excitation and fluorescent signals from ambient light. Digital-signal processing technique such as Fast Fourier Transformation (FFT) and signal averaging were implemented using low cost DSP chips to improve the signal-to-noise ratio (SNR) of very low intensity fluorescence signals using inexpensive photodetector/amplifier packages.

The invention provides a combination of a dichroic filter and implementation of a digital-signal processing technique thereby alleviating problems associated with fiber bending loss.

These and further and other objects and features of the invention are apparent in the disclosure, which includes the above and ongoing written specification, with the claims and the drawings.

DETAILED DESCRIPTION OF PREFERRED EMBODIMENTS

Figure 1:
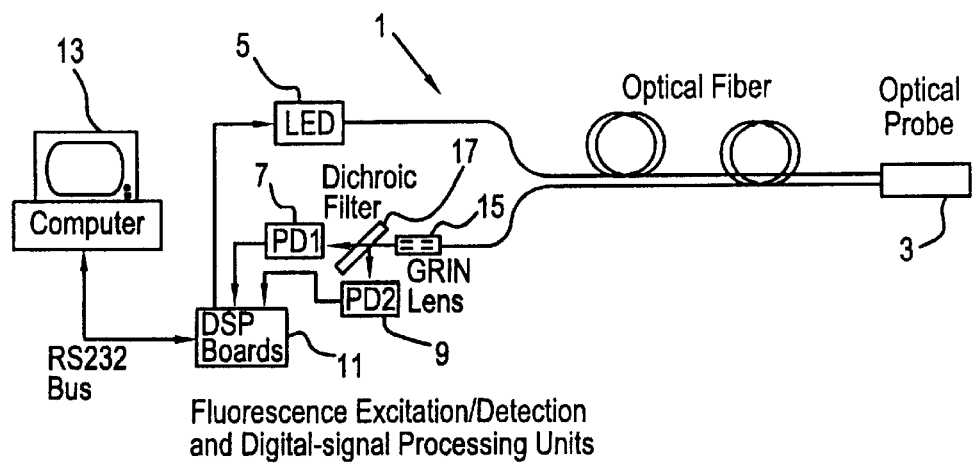
FIG. 1 is a schematic of fluorescence intensity based fiber-optic oxygen sensor.

A schematic diagram of the fluorescence-based fiber-optic oxygen sensor is shown in FIG. 1. The sensor system 1 consists of the optical sensor probe 3, the excitation light source 5 and detection electronics 7, 9, connected to digital-signal processing electronics 11 connected to a computer 13. The components are described in FIG. 1.

The use of optical fiber sensors to monitor dissolved oxygen concentration has been reviewed by LEINER, who noted that most optical sensors for oxygen concentration rely on dynamic quenching of fluorescence of suitable indicator dyes. For a homogeneous medium with single-component fluorescence decay, the intensities of fluorescence in the absence of oxygen, $I_O$, and in the presence of oxygen, $I$, are related through the Stern-Volmer equation as $$I_O/I = I + KQ \quad (1)$$

where Q, is the concentration of oxygen and K is the Stern-Volmer quenching constant.

To detect dissolved oxygen, a variety of different indicators, each with different excitation and emission wavelengths, has been used. These indicators include polycyclic aromatic hydrocarbons (PAHs) such as pyrene, fluoranthene, decacyclene, diphenylanthracene and benzo(ghi)perylene, whose fluorescence signals are efficiently quenched in the presence of oxygen and are soluble in silicone polymers. Another group of indicators is the transition metal complexes of ruthenium, osmium-iridium and platinum, which are more photostable and display relatively long fluorescence decay times.

The working principle of a fluorescence oxygen sensor is based on the quenching of fluorescence of a ruthenium complex by singlet oxygen atoms. Ruthenium Tris(2,2'-bipyridyl)dichloride which is commercially available has been frequently used in developing fiber-optic oxygen sensors. However, this compound suffers from drawbacks such as solubility in aqueous media and low quenching efficiency. Ruthenium (II) tris (4,7-diphenyl-1, 10-phenanthroline) (Ru(Ph$_2$phen)$_3$) dichloride is insoluble in aqueous media and has a larger solution Stern-Volmer quenching constant and larger quenching efficiency. This complex was synthesized for this work and the procedure for fabrication is described by WATTS and CROSBY.

Silicon rubber has been widely used as a matrix for $O_2$ probes due to its hydrophobicity and gas permeability. These probes have been shown to be accurate and precise for measuring oxygen concentrations in solution and in the gas phase. Aqueous acids, bases, oxidants and reductants do not penetrate the hydrophobic polymer and therefore do not affect the response. Gaseous interferents, such as $H_2S$, $N_2O$, halothane and fluorocarbons also do not affect the response. Silicone rubber RTV-118 (General Electric) was used to prepare sensor films by soaking the film in a methylene chloride solution of $Ru(Ph_2phen)_3Cl_2$. The film swelled in $CH_2Cl_2$ and took up the ruthenium complex. The concentration of the ruthenium complex in the film may be controlled by adjusting the concentration of $Ru(Ph_2phen)_3Cl_2$ in $CH_2Cl_2$. Tests of dye leaching were performed by soaking the ruthenium complex doped film in distilled water for a week. Then the distilled water was checked by UV/Vis spectrophotometry, and no absorption of this dye was observed indicating that the dye did not leach into water.

Fiber bending loss is compensated by using the ratio of the fluorescence and the excitation signal. A bright blue LED (Nichia America, USA) was used as the excitation light source (5 in FIG. 1). The excitation light was launched into a 1 mm diameter plastic optical fiber, and the dye-doped film was excited through a blue additive dichroic filter (Corion). The collection fiber was attached side-on to the dye-doped film, and the fluorescence signal was transmitted by the fiber to the detector assembly.

A graded refractive index (GRIN) lens (15 in FIG. 1) having 0.25 pitch was used to collimate the fluorescence signal and a yellow subtractive dichroic filter (Corion) 17 (FIG. 1) having cutoff wavelength at 550 nm was implemented to separate the residue excitation and fluorescence spectra. The two separated spectra were detected using two high-gain amplifier/detectors (Burr-Brown, Model OPT201).

Since an LED/photodetector combination was used, the total cost of the components is less than $300. The size of the system configuration was minimal. Since no laser was used in the package, the light source and detector fit into a package of dimensions 10×7×5 cm. Additional advantages of this oxygen sensor includes fast response time and no consumption of oxygen during measurement processes. The following section describes the implementation of the DSP technique to remove the influence of ambient room light and to reduce the influence of fiber bending losses.

Figure 2:
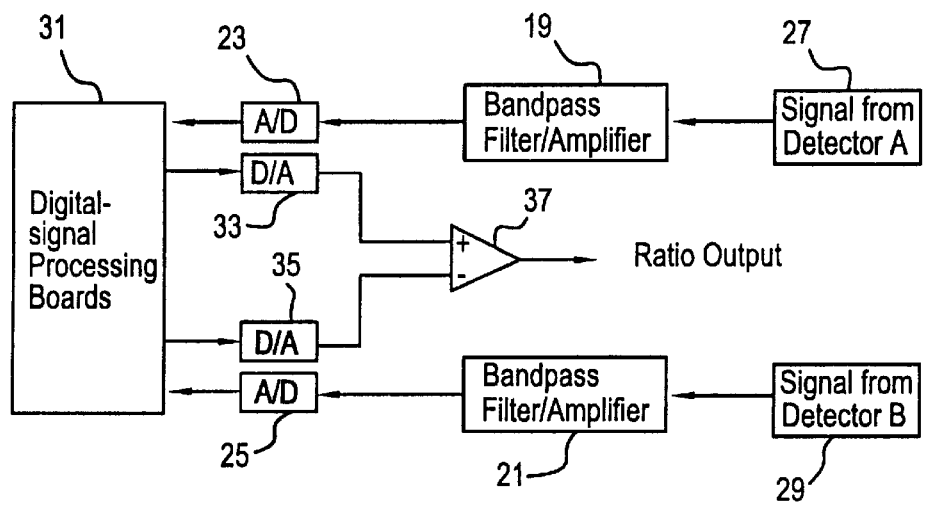
FIG. 2 is a block-diagram of digital-signal processing hardware.

The Texas Instruments TMS320C26 DSP Starter kit (DSK) was employed as the heart of the sensors' electronics. A simplified functional block diagram is shown in FIG. 2. The blue LED was driven at approximately 1.1 kHz. The fluorescence and the residue excitation signal were separated and detected as different channels A, B, 27, 29 in FIG. 2. The signal for each channel was fed into a 4 pole Butterworth active bandpass filter 19, 21, to reject interference noise signal from ambient light, and the analog signal was converted to digital signal by the DSK's onboard 12-bit analog-to-digital conversion interface circuit 23, 25.

A 256 point complex FFT was used to convert the time domain data into frequency domain by the DSP chip 31. The frequency window at 1.1 kHz was selected and the rest of the frequency data was set to zero. The resultant frequency spectrum was inverse FFT back to the time domain.

The ratio of the fluorescence and excitation channels is carried out by utilizing the logarithmic outputs of the DSP chips. Channels A and B 27, 29 denote the logarithm of the outputs from the fluorescence signal and the excitation signal, respectively.

The difference of the two channels $$\text{Channel A} - \text{Channel B} = \text{Log (Fluorescence)} - \text{Log (Excitation)} = \text{Log (Fluorescence/Excitation)} \quad (2)$$

thus, represents the logarithm of the ratio of fluorescence to the excitation signal. The difference of the two analog signals is easily implemented electronically using a unity gain difference amplifier circuit, which includes the digital-to-analog converter 33, 35 and microelectronics 37, in FIG. 2.

Figure 3:
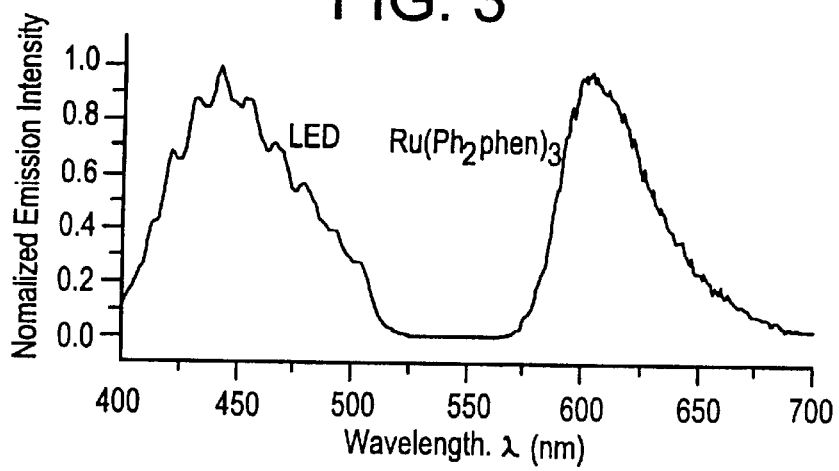
FIG. 3 depicts the emission spectra of blue LED and Ru(Ph$_2$phen)$_3$ in silicone matrices.

FIG. 3 shows the emission spectra of the blue LED after passing through the blue additive dichroic filter and $Ru(Ph_2Phen)_3$ embedded in silicone matrices. The large Stoke's shift of the fluorescence signal of the ruthenium complex makes it possible to efficiently separate the excitation source from the fluorescence using a dichroic filter at the center wavelength of 550 nm. The bright blue LED has an emission spectrum centered at 450 nm and is therefore suitable to excite the ruthenium complex.

Figure 4:
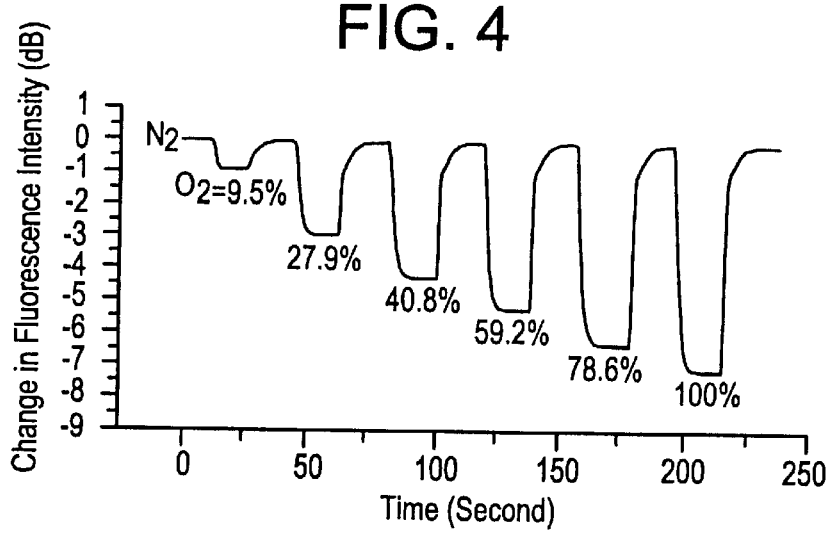
FIG. 4 shows the response of the fiber-optic sensor to various levels of oxygen.

FIG. 4 shows the ON/OFF response of the dye-doped silicone film to different oxygen levels. It shows that the response time of the sensor to pure oxygen or nitrogen is approximately 30 seconds. If fluorescence quenching is entirely diffusional, the fluorescence intensifies are related to the quencher concentration (oxygen concentration) by the Stern-Volmer equation (Equation 1).

Plots of $I_O/I$ or $(I_O/I-1)$ versus the quencher concentration should be linear if $O_2$ is the only quencher.

Figure 5:
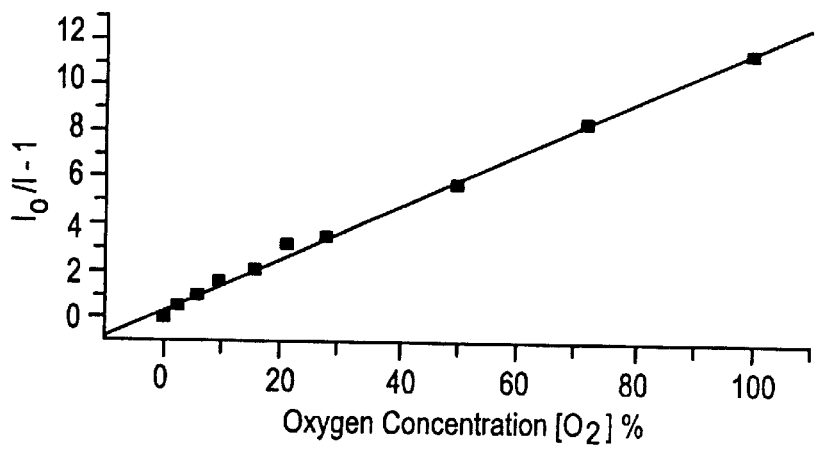
FIG. 5 is a Stern-Volmer Plot of fluorescence intensity versus oxygen concentration of the Ru(Ph$_2$phen)$_3$ doped silicone rubber.

FIG. 5 is a plot of $(I_O/I-1)$ versus percentage of oxygen. The linear relationship over the entire oxygen concentration range means that the film thickness and the dye distribution are homogeneous.

The stability and the signal-to-noise ratio of the system was improved by using the combination of an LED and digital-signal processing techniques. The stability of the system was investigated by measuring the fluorescence output of the sensor in air under laboratory conditions for a period of time. At 20° C. under ambient lighting condition, the short term (5 minutes) fluctuation of the oxygen sensor was 0.1% while the sensor fluctuation in one hour was 0.4%. The SNR of the sensor was improved through the use of digital signal averaging and FFT filters.

Figure 6A:
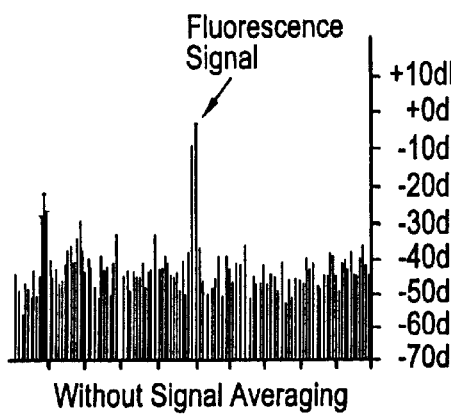
FIGS. 6A and 6B show the power spectrum oxygen observations of the fluorescence sensor without and with, respectively, signal averaging peaks of ambient fluorescence lamps.
Figure 6B:
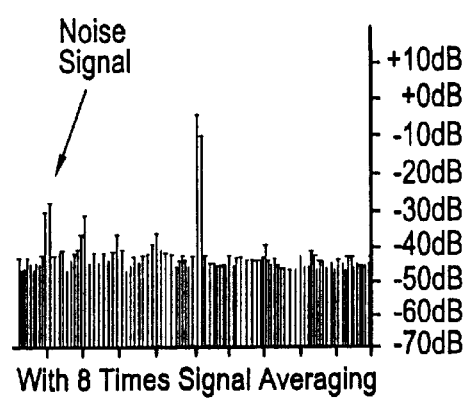

FIG. 6 shows the power spectrum of the fluorescence without averaging and with 8 times signal averaging. The background noise is significantly reduced by digital signal averaging. The presence of other noise frequencies are due to ambient fluorescent lamps.

The noise frequencies were efficiently removed by selecting a pass band in the power spectrum before transformation back to the time domain using inverse FFT. While active analog filtering may be implemented using an instrument such as a lock-in amplifier which has an approximate cost of more than $3,000, the present work demonstrates low light fluorescence signals are detected and stabilized using a DSP technique implemented using low cost DSP chips.

An experiment was carried out to demonstrate the ability of the ratiometric method to reduce the effect of bending loss in optical fiber. An assumption was made that the attenuation of the signal due to fiber bending loss is independent of the wavelength of the propagating light. Consequently, the attenuation will be the same for the fluorescence signal as well as the excitation light. The experiment consisted of bending either the excitation fiber or the collection fiber around circular cylinders of specific diameters while the fluorescence signal was measured using the instrumentation described earlier.

Figure 7:
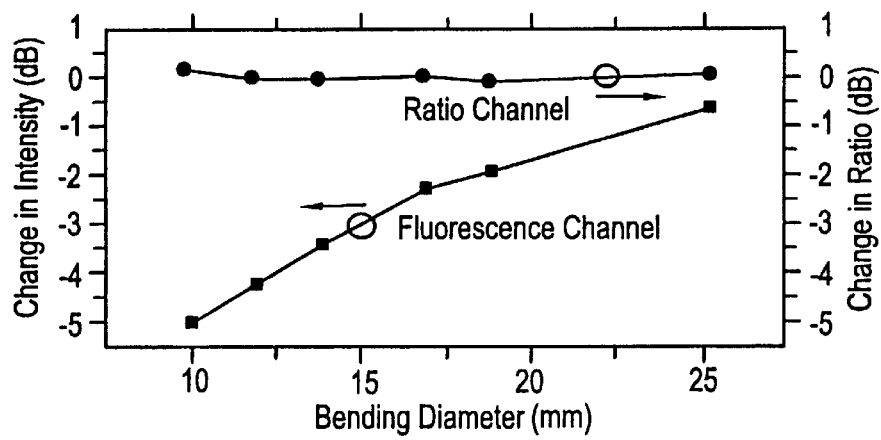
FIG. 7 shows the compensation of fiber bending loss when the excitation fiber is bent.

FIG. 7 shows the output of the fluorescence channel when the excitation fiber is bent at various diameters. These results show that while the fluorescence signal decreased by almost 5 dB when the fiber was bent to 10 mm, the ratio of the fluorescence signal to the excitation signal changed by 0.22 dB.

Figure 8:
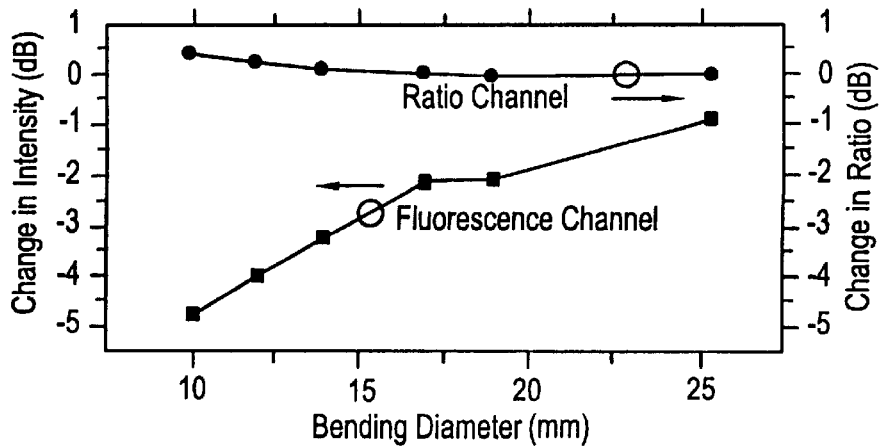
FIG. 8 is the compensation of fiber bending loss when the collection fiber is bent.

Similar results were obtained when the collection fiber was bent and the results are shown in FIG. 8. The decrease in the fluorescence signal was 4.8 dB when the fiber is bent to 10 mm, and the ratio of the fluorescence signal to the excitation signal changed by 0.42 dB.

The measurement of the output from the difference amplifier yields similar results. It was observed that the change in the ratio is more in the bending of the collection fiber than the excitation fiber. Although the ratiometric method in conjunction with DSP techniques alleviates the problem of fiber bending in fluorescence intensity based sensor, fiber bending loss cannot be completely eliminated.

One of the reasons for the inability to completely remove fiber bending loss is that bending loss may be a function of wavelength and therefore the fluorescence signal and the excitation wavelength have different attenuation in fiber bending.

A fluorescence intensity based oxygen sensor system capable of compensating the fiber-optic loss is demonstrated. The system utilizes a hardware implementation of digital-signal processing techniques using low-cost DSP clips to demonstrate an improvement in signal stability. A microcontroller controls and interprets the output from the DSP chips.

While the invention has been described with reference to specific embodiments, modifications and variations of the invention may be constructed without departing from the scope of the invention, which is defined in the following claims.

We claim:

1. A fiber-bending loss compensating system comprising a light source, a fiber-optic fluorescence sensor, a digital-signal processor connected to the sensor for enhancing a measurement of fluorescence signals and a computer for analyzing and outputting data relative to the signals, wherein the sensor is a fiber-optic oxygen sensor for measuring oxygen levels in a medium, further comprising a ruthenium complex in the oxygen sensor for quenching the fluorescence by singlet oxygen atoms.

2. The system of claim 1, wherein the light source is a modulated light-emitting diode excitation light source providing excitation signals, the sensor is an optical sensor probe, detectors connected to the probe, the digital-signal processor being connected to the probe, and the computer being connected to the processor.

3. The system of claim 2, further comprising the optical sensor probe having a polymer matrix resistant to acids, bases, oxidants, reductants, $H_2S$, $N_2O$, halothane and fluorocarbons for accurate and precise measurement of oxygen concentrations in liquids and gases.

4. The system of claim 3, wherein the polymer matrix is of silicon rubber material.

5. The system of claim 3, wherein the polymer matrix is a dye-doped film.

6. The system of claim 5, further comprising a blue additive dichroic filter for exciting the dye-doped film.

7. The system of claim 5, further comprising a collection fiber attached side-on to the dye-doped film.

8. The system of claim 7, wherein the collection fiber transmits the fluorescence signals to the detectors.

9. The system of claim 2, wherein a ratio of the fluorescence signals and the excitation signals provides compensation of a fiber bending loss.

10. The system of claim 2, wherein the excitation light source is a bright blue LED.

11. The system of claim 2, wherein excitation light is provided to a plastic optical fiber.

12. The system of claim 2, further comprising a graded refractive index lens for collimating the fluorescence signals.

13. The system of claim 2, further comprising a yellow subtractive dichroic filter for separating the residual excitation and fluorescence signals.

14. The system of claim 13, further comprising at least two high-gain amplifier/detectors for detecting the separated signals.

15. The system of claim 1, further comprising indicators having different excitation and emission wavelengths.

16. The system of claim 15, wherein the indicators are polycyclic aromatic hydrocarbons whose fluorescence signals are efficiently quenched in presence of oxygen and are soluble in silicone polymers.

17. The system of claim 16, wherein the hydrocarbons are selected from a group comprising pyrene, fluoranthene, decacyclene, diphenylanthracene and benzo(ghi)perylene.

18. The system of claim 15, wherein the indicators are transition metal complexes being more photostable and displaying longer fluorescence decay times.

19. The system of claim 18, wherein the complexes are selected from a group comprising ruthenium, osmium-iridium and platinum.

20. The system of claim 1, wherein the ruthenium complex is Ruthenium Tris(2,2'-bipyridyl)dichloride.

21. A fiber-bending loss compensating system comprising a light source, a fiber-optic fluorescence oxygen sensor for measuring oxygen levels, a ruthenium complex in the sensor for quenching fluorescence signals by singlet oxygen atoms, a digital-signal processor connected to the sensor for enhancing a measurement of the fluorescence signals and a computer for analyzing and outputting data relative to the signals, wherein the ruthenium complex is Ruthenium (II) tris (4,7-diphenyl-1,10-phenanthroline) dichloride.

* * * * *